US00PP35232P2

(12) United States Plant Patent
Hansen

(10) Patent No.: US PP35,232 P2
(45) Date of Patent: Jun. 20, 2023

(54) ***PULMONARIA* PLANT NAMED 'PINK-A-BLUE'**

(50) Latin Name: ***Pulmonaria* hybrid**
Varietal Denomination: Pink-a-Blue

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 17/803,788

(22) Filed: Nov. 22, 2022

(51) Int. Cl.
*A01H 6/00* (2018.01)
*A01H 5/02* (2018.01)

(52) U.S. Cl.
USPC ..... Plt./473

(58) Field of Classification Search
USPC ..... Plt./473
CPC ..... A01H 6/00; A01H 5/02
See application file for complete search history.

*Primary Examiner* — Keith O. Robinson

(57) ABSTRACT

A new and distinct hybrid of Lungwort plant named *Pulmonaria* 'Pink-a-Blue' is characterized by prominent silver spotting on deep green foliage and large campanulate flowers open deep-pink and mature to medium blue on numerous inflorescences. The new plants show excellent vigor and good mildew resistance.

2 Drawing Sheets

Botanical denomination: *Pulmonaria* hybrid.
Variety designation: 'Pink-a-Blue'.

STATEMENT REGARDING PRIOR DISCLOSURES UNDER 37 CFR 1.77(b)(6)

The information of the claimed plant, in the form of a photograph and brief description on websites operated by Walters Gardens, Inc. and Proven Winners® on Dec. 1, 2021, followed by a brief description and photograph in the "Walters Gardens 2022-2023 Catalog" first distributed on Jun. 8, 2022. Walters Gardens, Inc. and Proven Winners® both obtained the plant and all information about the plant from the inventor. The claimed plant was first sold on Jul. 11, 2022, to Garden Crossings and Plant Select by Walters Gardens, Inc., who obtained the plant and all information relating thereto, from the inventor. No plants of *Pulmonaria* 'Pink-a-Blue' have been sold in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to a new and distinct cultivar of *Pulmonaria* and was given the cultivar name of 'Pink-a-Blue'. *Pulmonaria* is in the family Boraginaceae. The new cultivar originated from a self-pollination on Apr. 14, 2015, of the proprietary, unreleased, unnamed hybrid known only by the breeder code 13-61-1 (not patented) in a research greenhouse at a perennial wholesale nursery in Zeeland, Mich., USA.

The new plant was initially asexually propagated at the same nursery in the summer of 2017 by division of the plant followed by plant tissue culture of the shoot tip in 2019. The result plants have shown themselves to be stable and true to type in successive generations of asexual propagation by division at the same nursery in Zeeland, Mich., and through shoot tip tissue culture.

SUMMARY OF THE INVENTION

The parent has foliage with fewer and smaller silver spots and a lighter green.

The nearest comparison plants known to the inventor include: 'Mrs. Moon' (not patented), 'Pretty in Pink' U.S. Plant Pat. No. 31,284, 'Trevi Fountain' U.S. Plant Pat. No. 13,047, 'May Bouquet' U.S. Plant Pat. No. 12,336, and 'Pierre's Pure Pink' (not patented).

'Mrs. Moon' has mature leaves that are broader, with larger and fewer spots, the green portion is lighter, and the mature flowers are darker blue. 'Pretty in Pink' has broader, deeper-pink flowers that retain a light pink color without turning blue, and the foliage has more silver coverage and less green. 'Trevi Fountain' has flowers that open more purple and less pink and mature to a strong violet. 'May Bouquet' has young flowers that are more purple and mature flowers that are a purplish-blue. 'Pierre's Pure Pink' has flowers that open a medium pink and mature to a light pink, and the foliage has smaller silver spots with less coverage on lighter green foliage.

*Pulinonaria* 'Pink-a-Blue' is distinct from all other lungwort plants known to the inventor by the following combined traits:

1. Medium pink flower buds on upright highly-branched stems in mid-spring;
2. Numerous inflorescences of dense panicles;
3. Large campanulate flowers initially open deep-pink and mature to a medium blue;
4. Deep green foliage with prominent silver spotting on both cauline leaves and basal leaves arising after flowering;

5. Foliage shows good mildew resistance;
6. Excellent vigor producing compact mounded habit.

BRIEF DESCRIPTION OF THE DRAWING

The photographs of the new plant demonstrate the unique traits of the new plant and the overall appearance. The colors are as accurate as reasonably possible with color reproductions. Variations in the ambient light spectrum, source, and direction may cause the appearance of minor variations in color. The accompanying photographs are of a three-year-old plant growing in a partially-shaded garden in Zeeland, Mich.

DETAILED PLANT DESCRIPTION

Figure 1:
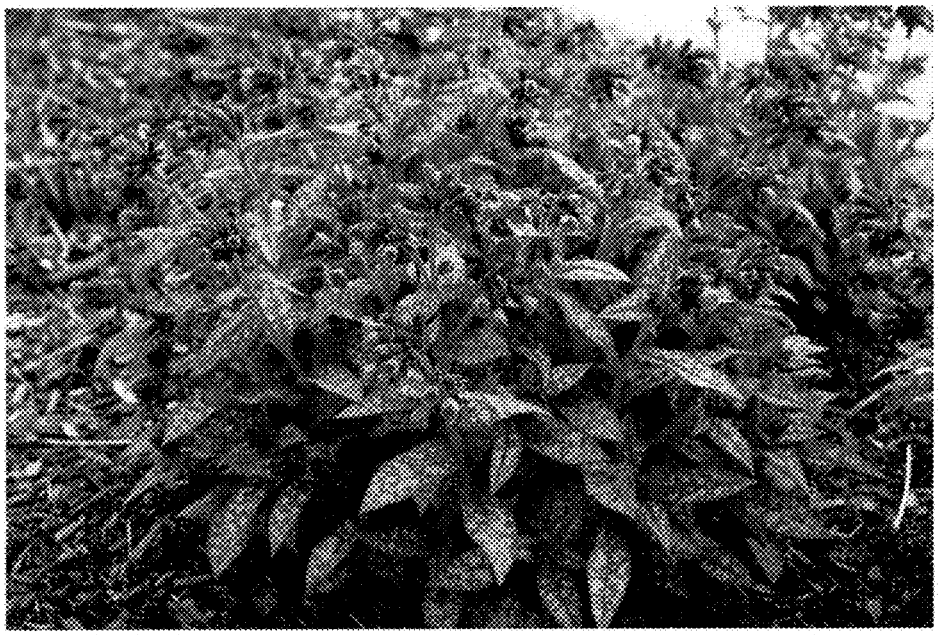
FIG. 1 shows the spring foliage and flowering habit of the new plant.
Figure 2:
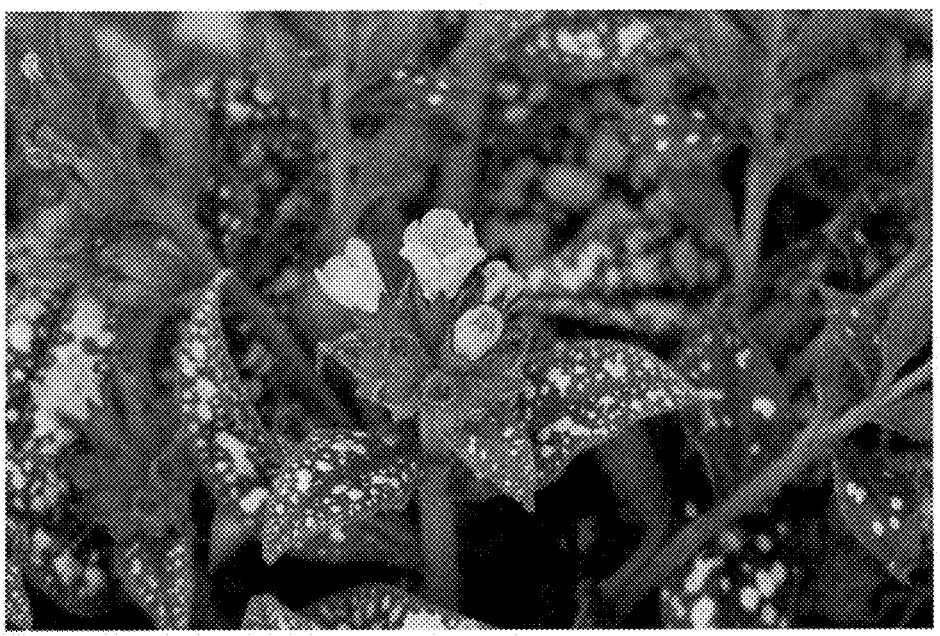
FIG. 2 shows a close-up of young and mature flowers and buds of the new plant.
Figure 3:
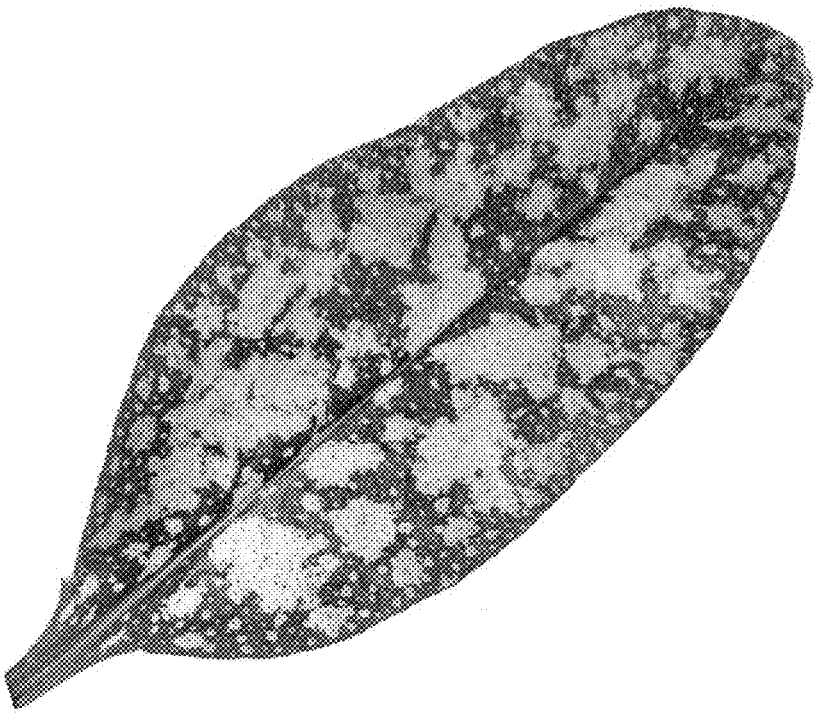
FIG. 3 shows a close-up of a mature leaf of the new plant.

The following is a detailed description of a three-year-old plant of 'Pink-a-Blue' as grown outdoors in a partially-shaded trial plot at a wholesale perennial nursery in Zeeland, Mich. Plants of the new cultivar have not been tested under all possible conditions. The phenotype may vary with changes in environment, climate, and cultural conditions without change however in the genotype. The color references are in accordance with the 2015 edition of The Royal Horticultural Society Colour Chart except where general color dictionary terms are used.

Parentage: Self-pollination of the proprietary hybrid 13-61-1;

Plant habit: Herbaceous, perennial forming low, multi-stemmed, flowering mound in spring followed in summer producing a clumping basal rosette;

Size: With spring flowering 54 cm wide and 33 cm tall; summer foliage size 68 cm wide and 32 cm tall;

Vigor: Excellent; produces rooted plantlet in tissue culture in about 14 to 20 days; fills a 3.8-liter container in about 10 weeks from tissue cultured plug;

Propagation: Division of the crown or tissue culture;

Roots: Fleshy, to about 3.0 mm thick; near white depending on soil type; color near 155D depending on soil minerals and makeup;

Leaves: In basal rosette; developing prior to flowers dehiscing; simple; oblanceolate; hispidulous adaxial and hispidulous to echinate abaxial; apex acute; base attenuate; margin entire, ciliolate; with spots on adaxial surface between 0.5 mm and frequently running together to about 30 mm in diameter;

Leaf size: To about 25 cm long and 8.5 cm wide at the center; average about 22.5 cm long and 7.5 cm wide;

Cauline leaf: Alternate; simple; ovate to oblanceolate; hispidulous abaxial and adaxial; acute apex; base attenuate, sessile, clasping; margin ciliolate and entire; with spots on adaxial surface between 0.5 mm and 5 mm diameter; to 8 cm long and 25 mm wide decreasing distally; average about eight cauline leaves per stem below flowers; cauline leaves and stems not persistent, drying after seed production;

Leaf color (basal and cauline): Adaxial between RHS NN137A and RHS 139A with irregular spotted silver portions nearest RHS 192A; abaxial between RHS 147D and RHS 147C;

Venation: Pinnate; only abaxial and adaxial midrib distinct; slightly depressed adaxial and costate abaxial; hispid to hispidulous abaxial and adaxial;

Vein color: Adaxial midrib nearest RHS 146D; abaxial midrib nearest RHS 146D;

Petiole description: Concavo-convex; scabrous;

Petiole size: To about 14 cm long and 12 mm wide at base; average about 11 cm long and 10 mm wide;

Petiole color: Adaxial and abaxial margin nearest RHS 137B; adaxial center between 145A and RHS 146D; abaxial midrib between 145A and RHS 146D, margin nearest RHS 146D;

Inflorescence: Terminal branched cyme; about 25 cymes per plant with 40 to 50 flowers per cyme, average 41 flowers per cyme; 2 or 3 branched with up to 8 flowers per branch; to 11 cm wide and flowering in distal 5 cm;

Flowering period: Beginning about mid-April and continuing for about four weeks;

Flower longevity: Individual flowers open for about four days;

Flower fragrance: None detected;

Peduncle: Cylindrical; hispidulous; about 34 cm long, about 5.0 mm diameter at base; upright;

Peduncle color: Blend between RHS 146D and RHS 146C;

Pedicel: Cylindrical; echinulate; to about 3 mm long and about 1 mm diameter elongating after flowering to about 8 mm long and 1.5 mm diameter; color nearest RHS 146D with moderate blush of nearest RHS 181C;

Flower bud: Tubular; to about 19 mm long and 6.5 mm wide at petals and calyx about 7 mm diameter;

Flower bud color: One day prior to opening calyx base nearest RHS 138B, center nearest RHS NN137B, and distally nearest RHS N186C with exposed petals between RHS 186A and RHS 186B;

Flower: Campanulate, actinomorphic, forming funnelform corolla; size 24 mm long and 16 mm wide;

Petals: Five; free in distal 7 mm, fused in basal 17 mm, with the basal 12 mm forming a tube; with rounded apices; margins minutely crenate; glabrous abaxial and adaxial except for adaxial pubescent with tufts of hairs about 1 mm long about 8 mm to 11 mm from base; about 24 mm long and 8 mm across midway between apex and fusion;

Petal color: Young adaxial basal 7 mm between RHS 157D and RHS NN155B, distal portion between RHS 186C and RHS 186B with a center stripe between RHS 93C and RHS 93B; mature abaxial basal 7 mm between RHS 157D and RHS NN155B, distal portion between RHS 186C and RHS 186B with a center stripe between RHS 93C and RHS 93B, and ring between tube and bell of between RHS N186C and RHS N186D; mature adaxial basal 7 mm between RHS 157D and RHS NN155B and distal portion nearest RHS 96C; mature abaxial proximal portion between RHS 157D and RHS NN155B, distal portion nearest RHS 96C, with a ring between tube and bell nearest RHS 96A;

Calyx description: Campanulate; about 17 mm long and 8 mm across at apex;

Sepals: Five; lanceolate; apices acute; about 17 mm long and 3 mm across at fusion, fused in basal about 9 mm; abaxial echinulate and adaxial hirsutulous;

Sepal color: Adaxial nearest RHS 147B; abaxial nearest RHS 137A with strong distal blush and faint proximal blush of nearest N186B to nearly solid RHS N186B at apex;

Gynoecium: One; pistil to about 12.5 mm long;

Ovary: Partially inferior, four-chambered; flattened globose to about 2 mm across and 1 mm tall; color between RHS 145A and RHS 146D;

Style: Cylindrical; glabrous; erect; about 9 mm long and about 0.5 mm diameter at base; color nearest RHS NN155B proximally and nearest RHS NN155C distally;

Stigma: Globose; to about 0.5 mm diameter; color between RHS 157D and RHS NN155B;

Androecium: Five;

Filament: Too short to be described;

Anther: Introrse; dorsifixed; longitudinal; oblong about 2.5 mm long and 0.5 mm diameter; color nearest RHS N186A;

Pollen: Abundant; color RHS NN155B;

Seed: To about four per flower, typically maturing to single seed; held within calyx; globose with rounded base and acute apex; about 1.0 mm diameter; color nearest RHS N199B;

Resistance to pests and diseases: *Pulmonaria* 'Pink-a-Blue' has good mildew resistance but has not shown any resistance or susceptibility beyond that common to other Lungwort.

Hardiness: The new plant is hardy from at least USDA hardiness zones 3 through 9.

I claim:

1. The new and distinct cultivar of *Pulmonaria* plant named 'Pink-a-Blue' as herein described and illustrated.

* * * * *